US007079249B2

(12) United States Patent
Nicolaides et al.

(10) Patent No.: US 7,079,249 B2
(45) Date of Patent: Jul. 18, 2006

(54) MODULATED REFLECTANCE MEASUREMENT SYSTEM WITH FIBER LASER TECHNOLOGY

(75) Inventors: Lena Nicolaides, Castro Valley, CA (US); Jeffrey T. Fanton, Los Altos, CA (US); Alex Salnik, Castro Valley, CA (US)

(73) Assignee: Therma-Wave, Inc., Fremont, CA (US)

( * ) Notice: Subject to any disclaimer, the term of this patent is extended or adjusted under 35 U.S.C. 154(b) by 416 days.

(21) Appl. No.: 10/453,146

(22) Filed: Jun. 3, 2003

(65) Prior Publication Data

US 2003/0234933 A1    Dec. 25, 2003

Related U.S. Application Data

(60) Provisional application No. 60/390,752, filed on Jun. 21, 2002.

(51) Int. Cl.
 *G01N 21/00* (2006.01)
 *G01N 21/55* (2006.01)
(52) U.S. Cl. .................... 356/432; 356/445
(58) Field of Classification Search ........ 356/364–369, 356/432, 445, 237.2, 237.3, 237.4, 237.5; 250/341.1, 225
 See application file for complete search history.

(56) References Cited

U.S. PATENT DOCUMENTS

| 4,999,014 | A   | 3/1991  | Gold et al. ............ 356/382 |
| 5,042,951 | A   | 8/1991  | Gold et al. ............ 356/369 |
| 5,111,326 | A * | 5/1992  | Ball .................... 359/244 |
| 5,166,752 | A   | 11/1992 | Spanier et al. ......... 356/369 |
| 5,329,357 | A * | 7/1994  | Bernoux et al. ........ 356/369 |
| 5,502,567 | A   | 3/1996  | Pokrowsky et al. ..... 356/367 |
| 5,608,526 | A   | 3/1997  | Piwonka-Corle et al. ... 356/369 |
| 5,610,712 | A   | 3/1997  | Schmitz et al. ........ 356/335 |
| 5,706,094 | A * | 1/1998  | Maris .................. 356/432 |
| 5,822,067 | A   | 10/1998 | Yanik .................. 356/368 |
| 5,999,544 | A   | 12/1999 | Petersen ............... 372/6 |
| 6,489,801 | B1* | 12/2002 | Borden et al. .......... 324/766 |
| 6,504,618 | B1* | 1/2003  | Morath et al. ......... 356/630 |

(Continued)

FOREIGN PATENT DOCUMENTS

EP        0 397 388        5/1990

(Continued)

OTHER PUBLICATIONS

D.G. Baker, "Monomode Fiber-Optic Design with Local-Area and Long-Haul Network Applications," published by Van Nostrand Reinhold Company, New York, 1978, p. 128.

(Continued)

*Primary Examiner*—Layla G. Lauchman
(74) *Attorney, Agent, or Firm*—Stallman & Pollock LLP

(57) ABSTRACT

A modulated reflectance measurement system includes two diode-based lasers for generating a probe beam and an intensity modulated pump beam. The pump and probe beams are joined into a collinear beam using a laser diode power combiner. One or more optical fibers are used to transport the beams either before and/or after they are combined. The collinear beam is focused through one or more lenses or other optical components for collimation. The collinear beam is then focused by an objective lens onto a sample. Reflected energy returns through an objective and is redirected by a beam splitter to a detector. A lock-in amplifier converts the output of the detector to produce quadrature (Q) and in-phase (I) signals for analysis. A processor uses the Q and/or I signals to analyze the sample.

3 Claims, 5 Drawing Sheets

U.S. PATENT DOCUMENTS

| | | | |
|---|---|---|---|
| 6,563,591 B1 * | 5/2003 | Maris | 356/496 |
| 6,958,814 B1 * | 10/2005 | Borden et al. | 356/432 |
| 2003/0076497 A1 * | 4/2003 | Wolf et al. | 356/369 |

FOREIGN PATENT DOCUMENTS

| | | |
|---|---|---|
| EP | 0 632 256 A1 | 6/1993 |
| WO | WO 96/29583 | 9/1996 |
| WO | WO 97/37265 | 10/1997 |
| WO | WO 01/55671 A1 | 8/2001 |

OTHER PUBLICATIONS

M. Young, "Optics and Lasers Including Fibers and Optical Waveguides," Fourth Revised Edition, published by Springer-Verlag, New York, 1993, pp. 260-261.

* cited by examiner

Fig. 5A
Fig. 5B
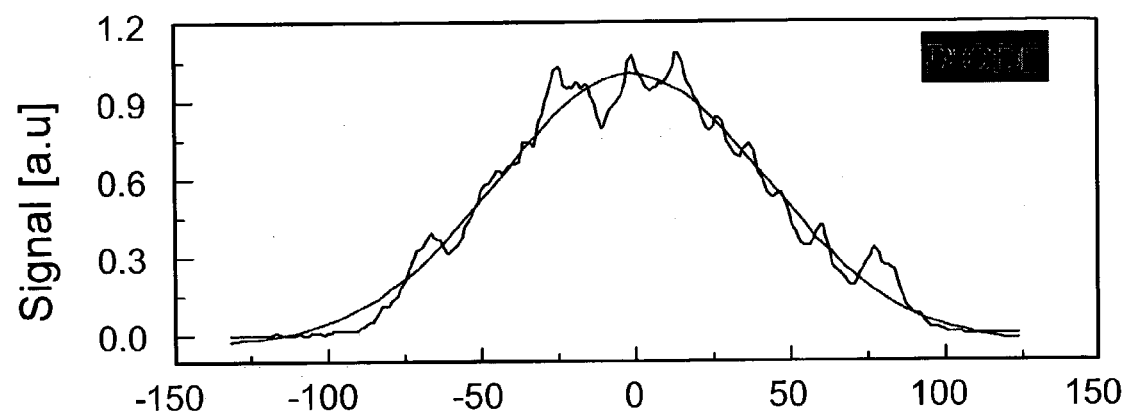
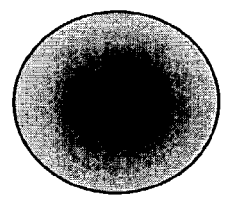
Fig. 6A
Fig. 6B
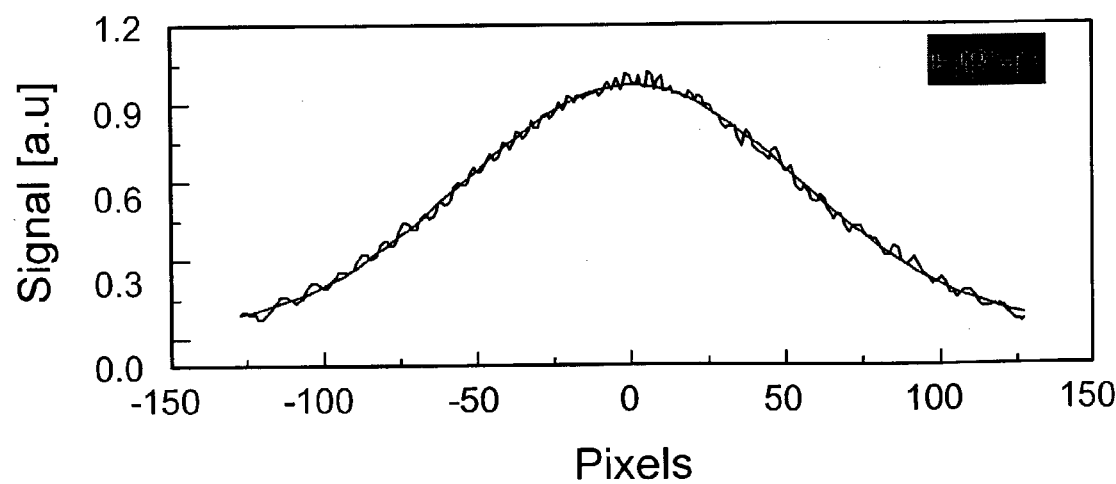

MODULATED REFLECTANCE MEASUREMENT SYSTEM WITH FIBER LASER TECHNOLOGY

PRIORITY CLAIM

The present application claims priority to U.S. Provisional Patent Application Ser. No. 60/390,752, filed Jun. 21, 2002, the disclosure of which is incorporated herein by reference.

TECHNICAL FIELD

The subject invention relates generally to optical methods for inspecting and analyzing semiconductor wafers and other samples. In particular, the subject invention relates to methods for increasing the accuracy and flexibility of systems that use modulated optical reflectivity to analyze semiconductor wafers.

BACKGROUND OF THE INVENTION

There is a great need in the semiconductor industry for metrology equipment that can provide high resolution, nondestructive evaluation of product wafers as they pass through various fabrication stages. In recent years, a number of products have been developed for the nondestructive evaluation of semiconductor samples. One such product has been successfully marketed by the assignee herein under the trademark Therma-Probe. This device incorporates technology described in the following U.S. Pat. Nos.: 4,634,290; 4,646,088; 5,854,710; 5,074,669 and 5,978,074. Each of these patents is incorporated herein by reference.

In the basic device described in the patents, an intensity modulated pump laser beam is focused on the sample surface for periodically exciting the sample. In the case of a semiconductor, thermal and plasma waves are generated in the sample that spread out from the pump beam s pot. These waves reflect and scatter off various features and interact with various regions within the sample in a way that alters the flow of heat and/or plasma from the pump beam spot.

The presence of the thermal and plasma waves has a direct effect on the reflectivity at the surface of the sample. As a result, subsurface features that alter the passage of the thermal and plasma waves have a direct effect on the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused collinearly with the pump beam and reflects off the sample. A photodetector is provided for monitoring the power of reflected probe beam. The photodetector generates an output signal that is proportional to the reflected power of the probe beam and is therefore indicative of the varying optical reflectivity of the sample surface.

The output signal from the photodetector is filtered to isolate the changes that are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

It can be proven theoretically that the overlap and pointing stability of each individual laser is important for accurate results. Therefore, these devices can be quite sensitive to the laser pointing stability. This problem is particularly acute when dealing with semiconductor lasers.

As shown in FIG. 1, and as described in U.S. Pat. No. 5,978,074, cited above, the current Therma-Probe system 100 uses a tracker mechanism to correct for the poor pointing stability of diode lasers. The tracker is a device used to optimize the overlap between the pump and probe lasers in the focusing plane (i.e., the sample). The tracker consists of a long focal length plano-convex lens with two motors to allow movement in both the x and y direction. The tracker is placed in front of the collimated pump laser and adjusts the pump laser output to match the output of the probe laser in the focusing plane.

The following optimization method is then used to correct for the pointing instability. The tracker is scanned first in x-direction and then in y-direction. At each incremental movement the thermal wave signal is recorded on a reference sample. A software routine finds the maximum value of the thermal wave signal at which time the tracker moves to the corresponding position. The tracker scanning function is repeated frequently during operation of the system to improve the pointing stability of the pump laser relative to the probe laser.

A drawback of this methodology is that pump laser effectively chases the probe beam. If the location of the probe beam drifts in a constant direction both lasers may be clipped at the focusing objective. Also, any "structure" in the pump or probe beam profile (which is typical of diode lasers), can lead to false maximums in the thermal wave signal, resulting in an error in pump/probe overlap. Another drawback of the methodology is that the tracker scanning is not performed in a 2-D plane (map) and thus prevents correction of non-symmetrical beams, which is usually the case of diode lasers.

To improve the quality of the probe beam, U.S. Pat. Nos. 6,049,220 and 6,489,801 (both to P. Borden et al.) describe a photothermal system that uses a fiber-coupled infrared probe laser. However, in these patents only one laser (probe) is shown to have a fiber connection that only partially improves the overall system performance.

For these reasons and others there is a need for a system that better optimizes the overlap between pump and probe lasers in modulated reflectance measurement systems. This is particularly important as semiconductor geometries continue to shrink and accurate measurements become increasing difficult to achieve.

SUMMARY

The present invention provides a modulated reflectance measurement system that reduces alignment errors between pump and probe beams. The measurement system includes a probe laser and a pump laser, each producing monochromatic light at a different spectrum. A modulator is used to cause the pump laser to have an intensity modulated output, referred to as the pump beam. The probe laser produces an output that is typically non-modulated (i.e., constant intensity). This output is referred to as the probe beam.

The output of the probe laser and the output of the pump laser are joined into a collinear beam using a laser diode power combiner. An optical fiber transports the now collinear probe and pump beams from the laser diode power combiner to a lens or other optical device for collimation. Once collimated, the collinear beam is focused on a sample by an objective lens.

A reflected portion of the collinear probe and pump beams is redirected by a beam splitter towards a detector. The detector measures the energy reflected by the sample and forwards a corresponding signal to a filter. The filter typically includes a lock-in amplifier that uses the output of the detector, along with the output of the modulator to produce quadrature (Q) and in-phase (I) signals for analysis. A processor typically converts the Q and I signals to amplitude and/or phase values to analyze the sample. In other cases, the Q and I signals are used directly.

For another implementation of the measurement system, separate optical fibers are used to collect the pump and probe beams from their laser sources. The optical fibers transport the pump and probe beams to an optical combiner. The optical combiner joins the pump and probe beams into a collinear beam that is transported by another optical fiber to a lens or other optical device for collimation. As before, the collinear beam is reflected by the sample and analyzed using a detector, filter and processor.

In another implementation of the measurement system, separate optical fibers are used to collect the pump and probe beams from their laser sources. One of these fibers transports the pump beam to a tracking mechanism. The second optical fiber transports the probe beam to a dichroic mirror. The dichoric mirror also collects the pump beam as it leaves the tracking mechanism. The two beams are joined into a collinear beam and focused onto a sample by an objective lens. As before, the collinear beam is reflected by the sample and analyzed using a detector, filter and processor.

BRIEF DESCRIPTION OF THE DRAWINGS

FIG. 5A is cross-sectional diagram of the combined pump and probe beam produced by the prior art modulated reflectance measurement system of FIG. 1.

FIG. 5B is graph showing signal strength as a function of position for the cross-section of FIG. 5A.

FIG. 6A is cross-sectional diagram of the combined pump and probe beam produced by the modulated reflectance measurement systems of FIG. 2.

FIG. 6B is graph showing signal strength as a function of position for the cross-section of FIG. 6A.

DETAILED DESCRIPTION OF THE PREFERRED EMBODIMENTS

Figure 2:
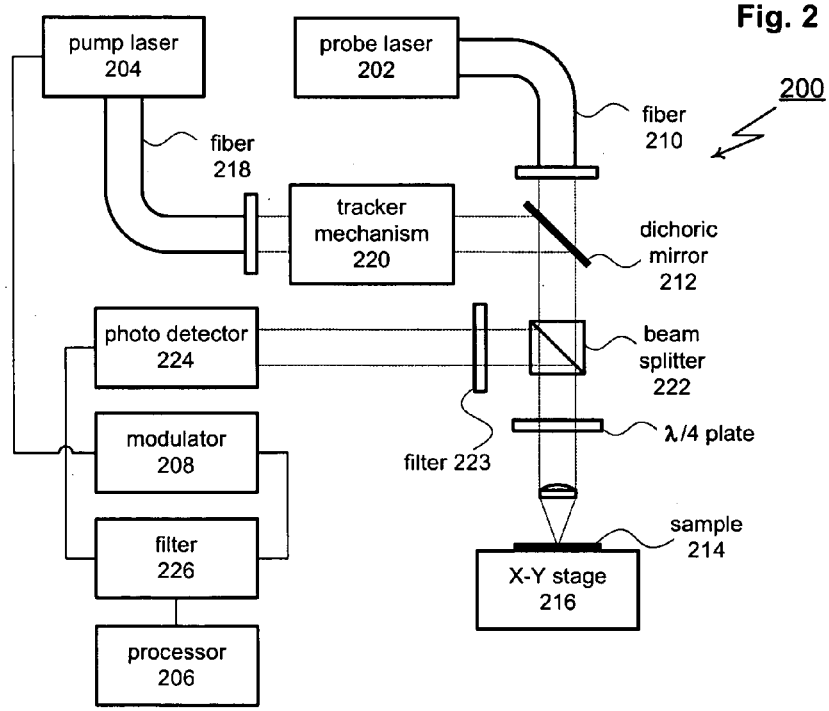
FIG. 2 is a block diagram of a modulated reflectance measurement system that uses optical fibers to transport pump and probe laser outputs.

The present invention provides a modulated reflectance measurement system that reduces alignment errors between pump and probe beams. In FIG. 2, a first possible implementation for the modulated reflectance measurement system is shown and generally designated 200. As shown, modulated reflectance measurement system 200 includes a probe laser 202 and a pump laser 204. Each laser 202, 204 is typically monochromatic and each laser 202, 204 typically operates at a different spectrum. Lasers 202, 204 are generally diode-based or diode-pumped semiconductor lasers. Solid state laser diodes are available that have outputs throughout the entire visible spectrum as well as in the infrared and near UV. Lasers 202, 204 are controlled by a processor 206 and a modulator 208. Modulator 208 causes pump laser 204 to have an intensity modulated output, referred to as the pump beam. Probe laser 202 produces an output that is typically non-modulated (i.e., constant intensity). This output is referred to as the probe beam.

As the probe beam leaves probe laser 202, it is collected by an optical fiber 210. Optical fiber 210 is typically single mode and directs the probe beam through a dichroic mirror 212 towards a sample 214. Sample 214 is positioned on an X-Y stage 216 allowing sample to be moved in translation relative to the probe beam. As the pump beam leaves pump laser 204, it is collected by a second optical fiber 218. Optical fiber 218 is typically single mode and directs the pump beam to a tracking mechanism 220. After leaving tracking mechanism 220, the pump beam is redirected by dichroic mirror 212. The redirection aligns the pump beam to be collinear with the probe beam as the probe beam travels towards sample 214.

After striking sample 214, the reflected probe beam is redirected by a beam splitter 222 towards a detector 224. Prior to reaching detector 224 the combined reflected light is passed through a filter 223. Filter 223 functions to remove pump beam light allowing the probe beam light to fall on the photodetector 224. Detector 224 measures the energy reflected by sample 214 and forwards a corresponding signal to a filter 226. Filter 226 typically includes a lock-in amplifier that uses the output of detector 224, along with the output of modulator 208 to produce quadrature (Q) and in-phase (I) signals for analysis. Processor 206 typically converts the Q and I signals to amplitude and/or phase values to analyze the sample. In other cases, the Q and I signals are used directly.

The use of optical fiber to deliver light from both probe laser 202 and pump laser 204 improves the individual pointing stability of each laser as well as the beam structure and circularity (symmetry) of the probe and pump beams. In practice, the pointing stability can be less than 1 μrad/° C.

Figure 1:
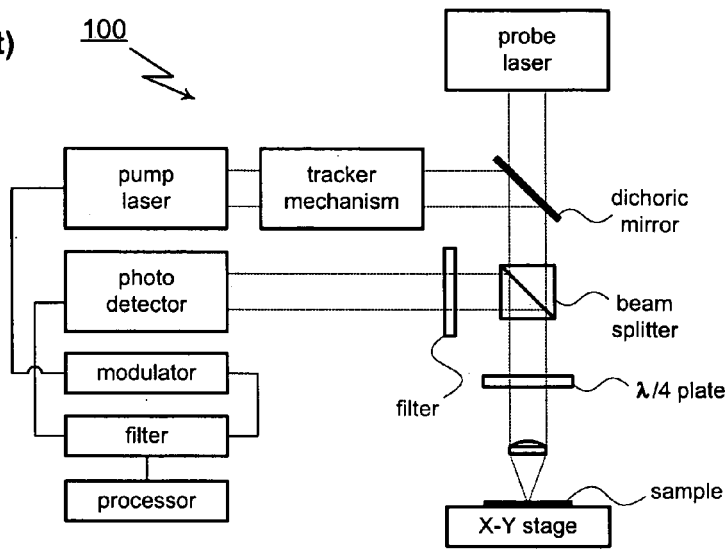
FIG. 1 is a block diagram of a prior art modulated reflectance measurement system.

The inventors herein have implemented a system as illustrated in FIG. 2. In this system the diode lasers of FIG. 1 are replaced with fiber-coupled diode lasers as seen in FIG. 2. In FIG. 2, two laser diodes 202 and 204 are each fiber-coupled to a polarization-maintaining and single mode fiber, 210 and 218. The assembly of the laser diodes 202 or 204 with coupling fiber 210 or 218, respectively, is usually referred to as a "pig-tailed laser fiber" and is provided as a complete assembly from Point-Source, Southhampton, UK. The diode pin-outs and the driving current requirements of the new pig-tailed laser fibers are identical to the old diode lasers of FIG. 1. This served as the basis to a retro-fit design enabling the new fiber-coupled diode lasers to be interfaced to the old PCB boards and to thus maintain the same communication interface as the old system. In the old system the diode laser package included the PCB board, diodes and collimation optics in one assembly which then directed each output beam to a dichoric splitter (FIG. 1). In the retro-fit design the PCB boards with the pigtail diodes are placed in one assembly 1m away from the usual optical configuration. A 1m flexible stainless steel jacket is strain-reliefed into a 1m coiled bare fiber which then guides the beam through an FC connector onto the collimating optics. The 1m coiled bare fiber and collimating optics are now placed in the same optical path of the old diode lasers and the beam output from each collimating optics is directed to the dichroic splitter, 212.

Figure 3:
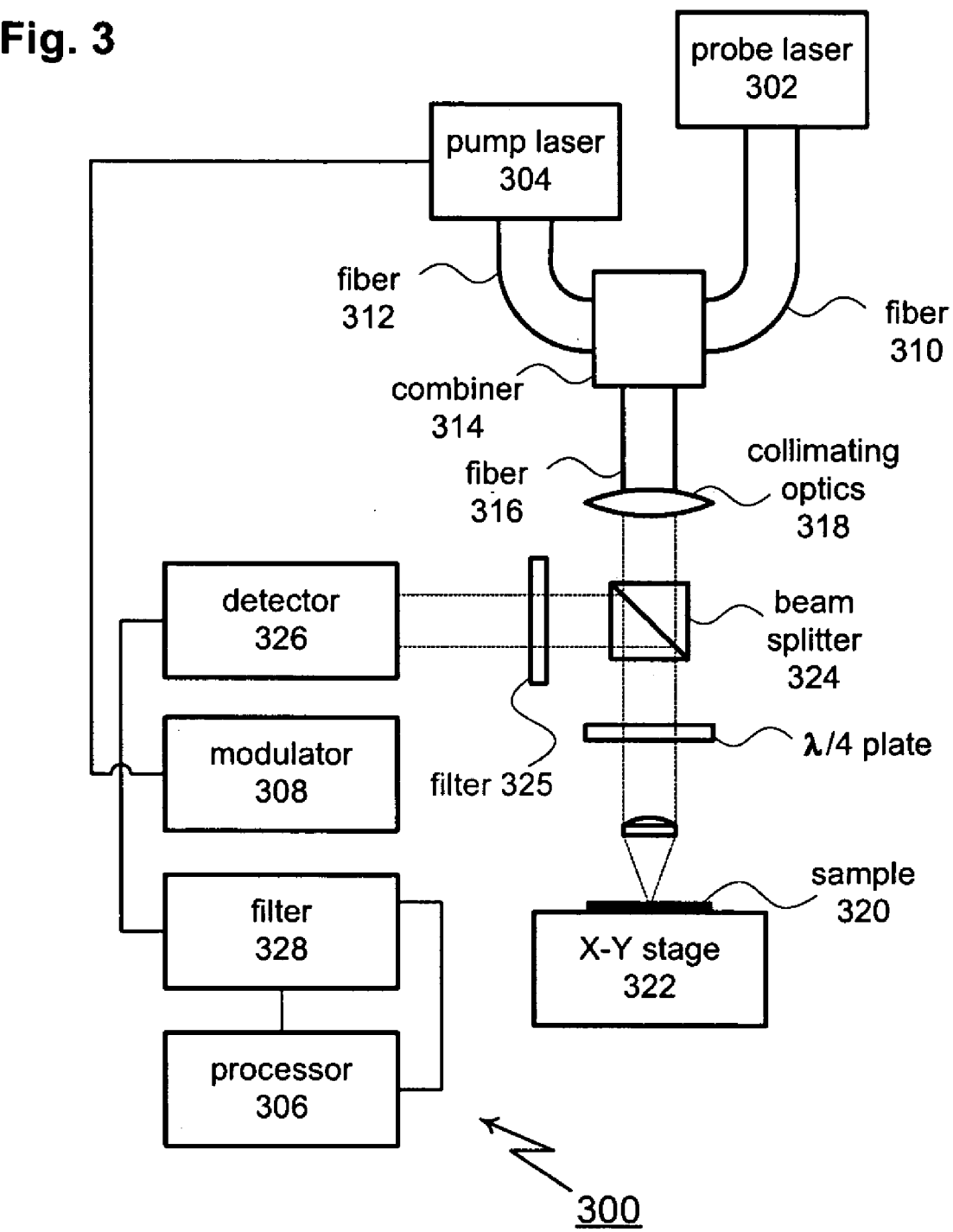
FIG. 3 is a block diagram of a modulated reflectance measurement system that uses optical fibers in combination with an optical combiner to transport pump and probe laser outputs.

In FIG. 3, a second possible implementation for the modulated reflectance measurement system is shown and generally designated 300. As shown, modulated reflectance measurement system 300 includes a probe laser 302 and a pump laser 304. Each laser 302, 304 is typically monochromatic and each laser 302, 304 typically operates at a different spectrum. Lasers 302, 304 are generally diode-based or diode-pumped semiconductor lasers. Solid state laser diodes are available that have outputs throughout the entire visible spectrum as well as in the infrared and near UV. Lasers 302, 304 are controlled by a processor 306 and a modulator 308. Modulator 308 causes pump laser 304 to have an intensity modulated output, referred to as the pump beam. Probe laser 302 produces an output that is typically non-modulated (i.e., constant intensity). This output is referred to as the probe beam.

The probe beam output of probe laser 302 and pump beam output of pump laser 304 are collected by optical fibers 310 and 312, respectively. The beams from fibers 310 and 312 are collimated and direct the probe and pump beams to a combiner 314. The beam combiner typically includes a dichroic element. The now collinear probe and pump beams leave combiner 314 and are focused into fiber 316. One suitable fiber optic beam combiner is manufactured by OZ Optics of Canada, part number FOBS-12P. Fiber 316 directs the collinear beams through collimating optics 318 to sample 320. Sample 320 is positioned on an X-Y stage 322 allowing sample to be moved in translation relative to the collinear beams.

After striking sample 320, a reflected portion of the collinear probe and pump beams is redirected by a beam splitter 324 through filter 325 and onto detector 326. Detector 326 measures the energy reflected by sample 320 and forwards a corresponding signal to a filter 328. Filter 328 typically includes a lock-in amplifier that uses the output of detector 326, along with the output of modulator 308 to produce quadrature (Q) and in-phase (I) signals for analysis. Processor 306 typically converts the Q and I signals to amplitude and/or phase values to analyze the sample. In other cases, the Q and I signals are used directly.

In general, modulated reflectance measurement system 300 provides the same combination of pointing stability, beam structure and beam circularity (symmetry) described for the implementation of FIG. 2. In this case, however, the use of combiner 314 means that there is no need for the tracking mechanism used in the implementation of FIG. 2 and other systems.

Figure 4:
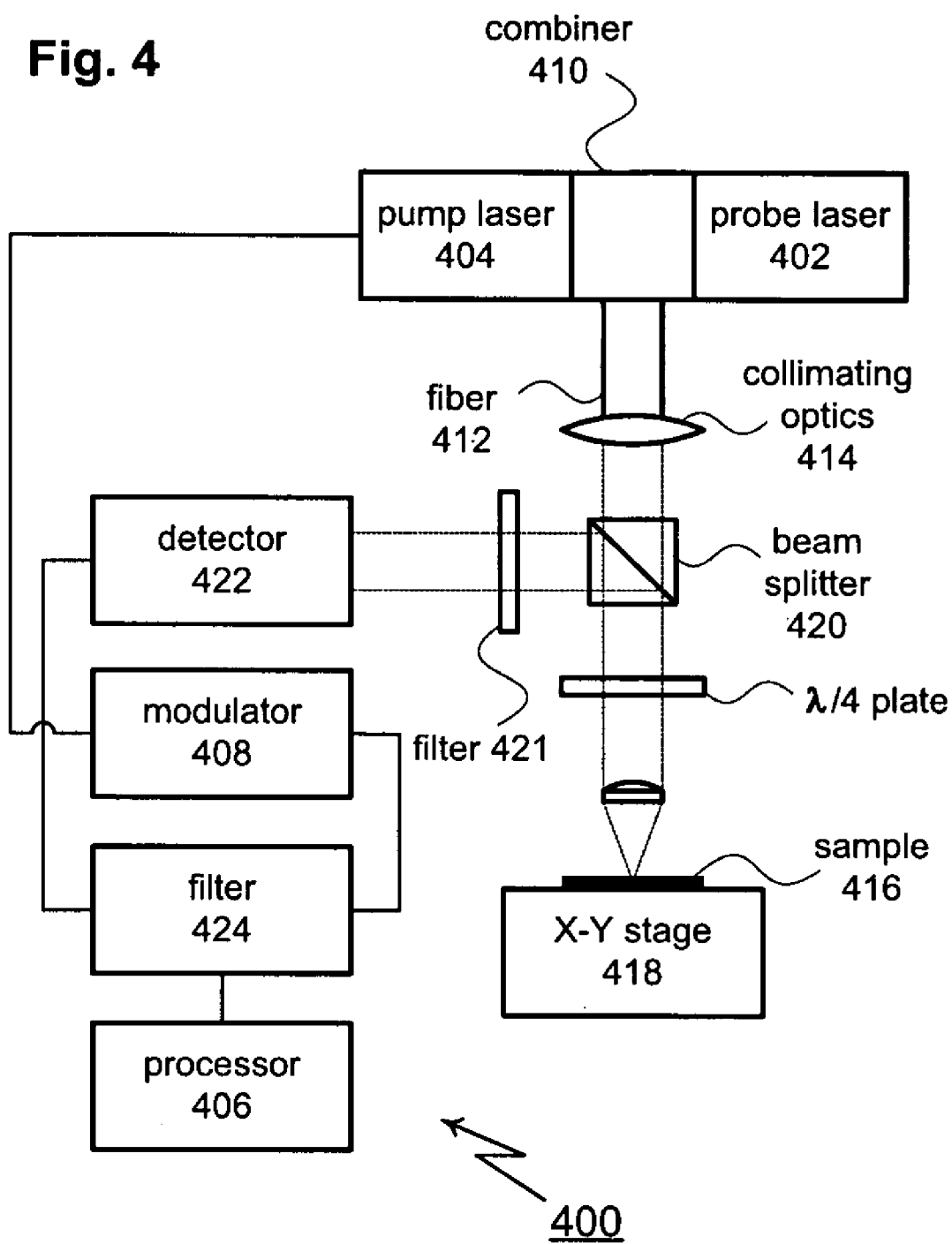
FIG. 4 is a block diagram of a modulated reflectance measurement system that uses a laser diode power combiner and an optical fiber to transport pump and probe laser outputs.

In FIG. 4, a third possible implementation for the modulated reflectance measurement system is shown and generally designated 400. As shown, modulated reflectance measurement system 400 includes a probe laser 402 and a pump laser 404. Each laser 402, 404 is typically monochromatic and each laser 402, 404 typically operates at a different spectrum. Lasers 402, 404 are generally diode-based or diode-pumped semiconductor lasers. Solid state laser diodes are available that have outputs throughout the entire visible spectrum as well as in the infrared and near UV. Lasers 402, 404 are controlled by a processor 406 and a modulator 408. Modulator 408 causes pump laser 404 to have an intensity modulated output, referred to as the pump beam. Probe laser 402 produces an output that is typically non-modulated (i.e., constant intensity). This output is referred to as the probe beam.

The probe beam output of probe laser 402 and pump beam output of pump laser 404 are collimated into a collinear beam using a laser diode power combiner 410. The now collinear probe and pump beams leave combiner 410 and are focused into fiber 412. One suitable laser power combiner is manufactured by OZ Optics of Canada, part number ULBS-11P. The fiber 412 directs the collinear beams through collimating optics 414 to sample 416. Sample 416 is positioned on an X-Y stage 418 allowing sample to be moved in translation relative to the collinear beams.

After striking sample 416, a reflected portion of the collinear probe and pump beams is redirected by a beam splitter 420 through filter 421 and onto detector 422. Detector 422 measures the energy reflected by sample 416 and forwards a corresponding signal to a filter 424. Filter 424 typically includes a lock-in amplifier that uses the output of detector 422, along with the output of modulator 408 to produce quadrature (Q) and in-phase (I) signals for analysis. Processor 406 typically converts the Q and I signals to amplitude and/or phase values to analyze the sample. In other cases, the Q and I signals are used directly.

In general, modulated reflectance measurement system 400 provides the same combination of pointing stability, beam structure and beam circularity (symmetry) described for the implementations of FIG. 2 and 3. In this case, however, the use of laser diode power combiner 410 reduces the number of optical fibers required.

For the purposes of comparison, FIG. 5A shows a typical combined pump and probe beam as produced by the modulated reflectance measurement system of FIG. 1. As demonstrated in that figure, the combined beam is elliptical and astigmatic. This non-Gaussian output is shown graphically in FIG. 5B. As may be appreciated, there are numerous deviations from the ideal output. FIG. 6A and 6B repeat the same demonstration for the combined output beams produced by modulated reflectance measurement system 200. As shown in FIG. 6A, the combined beam produced by these devices is substantially circular and, as shown in FIG. 6B, substantially Gaussian.

Figure 7:
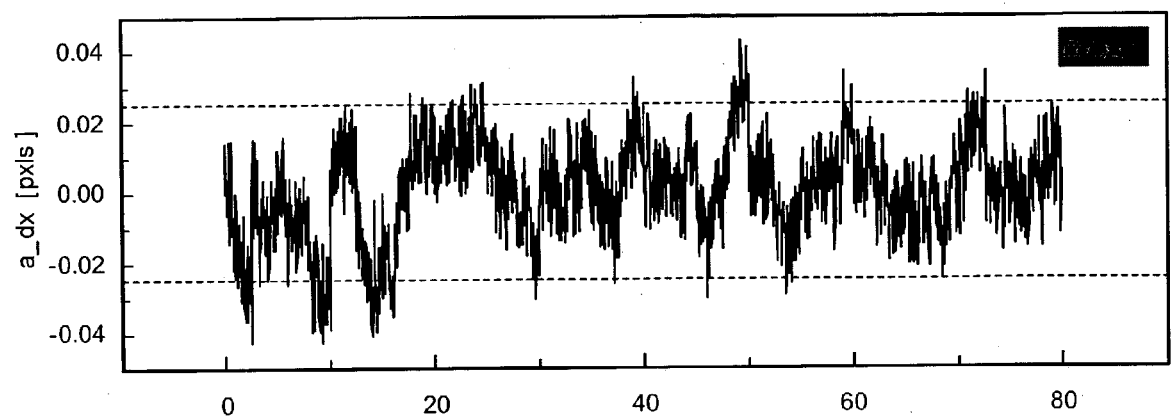
FIG. 7 is graph showing laser pointing stability as a function of time of the prior art modulated reflectance measurement system of FIG. 1.
Figure 8:
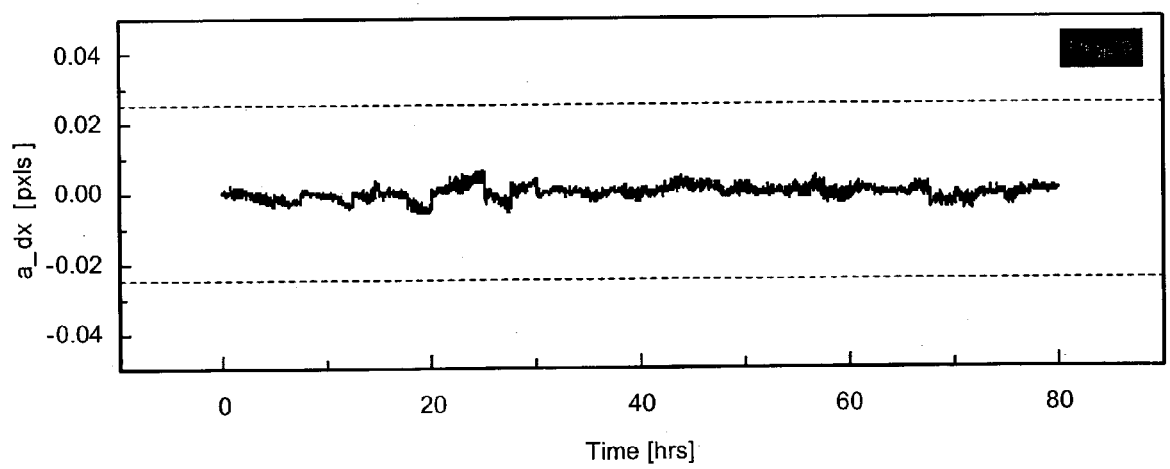
FIG. 8 is graph showing laser pointing stability as a function of time of the modulated reflectance measurement systems of FIGS. 2, 3 and 4.

FIG. 7 continues the comparison by showing the pointing stability of the combined pump and probe beam as produced by the modulated reflectance measurement system of FIG. 1. As demonstrated in that figure, the alignment between the pump and probe beams varies over time. This is due, in part to thermal cavity effects in the laser diodes that create the pump and probe beam. The thermal cavity effects result in small deviations in beam direction. As shown in FIG. 8, the fiber configuration used by modulated reflectance measurement system 200 greatly decreases this time varying quality. The result is a system in which the laser output is relative stable, greatly reducing the need for active correction of beam position or other compensating measures.

What is claimed is:

1. A measurement system for evaluating a sample comprising:
    a first diode laser generating an intensity modulated pump laser beam;
    a second diode laser generating a probe laser beam;
    a combiner, with the output of said first diode laser being coupled to said combiner by mounting said first diode laser directly to the combiner and with the output of said second diode laser being coupled to said combiner by mounting said second diode laser directly to the combiner;

a fiber operatively connected to said combiner, said combiner being arranged to combine the pump and probe laser beams and focus the combined laser beams into said fiber;

an objective lens positioned to focus the combined laser beams exiting the fiber onto the surface of the sample, with the pump laser beam periodically exciting a region of the sample surface, the objective lens also gathering a portion of the combined laser beams that are reflected from the periodically excited region;

a detector for monitoring the reflected portion of the probe laser beam and generating output signals corresponding thereto;

a filter for filtering the output signals; and a processor for evaluating the sample based on the filtered output signals.

2. A system as recited in claim 1 wherein said pump and probe laser beams are collimated into said beam combiner.

3. A measurement system for evaluating a sample comprising:

a first diode laser generating a pump laser beam;

a modulator connected to said first diode laser to cause said first laser to generate an intensity modulated output;

a second diode laser generating a probe laser beam;

a combiner, with the output of said first diode laser being coupled to said combiner by mounting said first diode laser directly to the combiner and with the output of said second diode laser being coupled to said combiner by mounting said second diode laser directly to the combiner;

a fiber operatively connected to said combiner, said combiner being arranged to combine the pump and probe laser beams and focus the combined laser beams into said fiber, said pump and probe laser beam being collimated into said beam combiner;

an objective lens positioned to focus the combined laser beams exiting the fiber onto the surface of the sample, with the pump laser beam periodically exciting a region of the sample surface, the objective lens also gathering a portion of the combined laser beams that are reflected from the periodically excited region;

a filter in the path of the combined reflected beams for blocking the pump laser beam;

a detector for monitoring the reflected portion of the pump laser beam;

a lock-in amplifier connected to the modulator and the detector for generating in-phase and quadrature signals; and a processor connected to the lock-in amplifier for generating amplitude and/or phase values based on the in-phase and quadrature signals, said amplitude and/or phase values used to evaluate the sample.

* * * * *